United States Patent
Hamacher et al.

(10) Patent No.: US 10,124,168 B2
(45) Date of Patent: Nov. 13, 2018

(54) SYSTEM FOR COMBINED NEURAL AND ACOUSTIC HEARING STIMULATION

(71) Applicant: ADVANCED BIONICS AG, Staefa (CH)

(72) Inventors: Volkmar Hamacher, Hannover (DE); Josef Chalupper, Paunzhausen (DE)

(73) Assignee: Advanced Bionics AG, Staefa (CH)

( * ) Notice: Subject to any disclaimer, the term of this patent is extended or adjusted under 35 U.S.C. 154(b) by 12 days.

(21) Appl. No.: 15/319,734

(22) PCT Filed: Jul. 7, 2014

(86) PCT No.: PCT/EP2014/064436
§ 371 (c)(1),
(2) Date: Dec. 16, 2016

(87) PCT Pub. No.: WO2016/004970
PCT Pub. Date: Jan. 14, 2016

(65) Prior Publication Data
US 2017/0128723 A1    May 11, 2017

(51) Int. Cl.
| | | |
|---|---|---|
| *A61N 1/00* | (2006.01) | |
| *A61N 1/36* | (2006.01) | |
| *A61N 1/05* | (2006.01) | |
| *H04R 25/00* | (2006.01) | |

(52) U.S. Cl.
CPC ....... *A61N 1/36032* (2013.01); *A61N 1/0541* (2013.01); *A61N 1/36128* (2013.01); *H04R 25/35* (2013.01); *H04R 2225/41* (2013.01); *H04R 2225/67* (2013.01)

(58) Field of Classification Search
CPC .............. A61N 1/0541; A61N 1/36032; A61N 1/36128; H04R 25/35; H04R 2225/41; H04R 2225/67
See application file for complete search history.

(56) References Cited

U.S. PATENT DOCUMENTS

| | | |
|---|---|---|
| 6,157,861 A | 12/2000 | Faltys et al. |
| 6,355,064 B1 | 3/2002 | Peeters et al. |
| 6,862,359 B2 | 3/2005 | Nordqvist et al. |
| 7,961,898 B2 | 6/2011 | Van den Heuvel |
| 8,155,747 B2 | 4/2012 | Faltys et al. |

(Continued)

FOREIGN PATENT DOCUMENTS

| | | |
|---|---|---|
| DE | 19542961 | 5/1997 |
| EP | 2635046 | 9/2013 |

(Continued)

OTHER PUBLICATIONS

International Search Report and Written Opinion received in International Application No. PCT/US14/051087, dated Dec. 23, 2014.

(Continued)

*Primary Examiner* — Mallika D Fairchild
(74) *Attorney, Agent, or Firm* — ALG Intellectual Property, LLC (57) ABSTRACT

There is provided a hearing assistance system comprising an auditory prosthesis device for neural stimulation of a patient's hearing at one of the patient's ears and a hearing aid for acoustic stimulation of the patient's hearing at the same one or the other one of the patient's ears.

35 Claims, 8 Drawing Sheets

(56) References Cited

U.S. PATENT DOCUMENTS

| | | |
|---|---|---|
| 8,565,889 B2 | 10/2013 | Spitzer |
| 8,571,674 B2 | 10/2013 | Nicolai et al. |
| 8,644,535 B2 | 2/2014 | Steinbuss |
| 8,644,536 B2 | 2/2014 | Van den Heuvel |
| 9,179,231 B2 | 11/2015 | Johnston et al. |
| 2004/0047474 A1 | 3/2004 | Vries et al. |
| 2005/0036637 A1 | 2/2005 | Janssen |
| 2005/0261748 A1 | 11/2005 | van Dijk |
| 2006/0089561 A1 | 4/2006 | Eder et al. |
| 2007/0043403 A1 | 2/2007 | Blamey et al. |
| 2007/0147624 A1 | 6/2007 | Fischer |
| 2007/0280494 A1 | 12/2007 | Hamacher |
| 2008/0107296 A1 | 5/2008 | Bachler et al. |
| 2008/0267434 A1 | 10/2008 | Schumaier |
| 2009/0264962 A1* | 10/2009 | Faltys .................. H04R 25/70 607/57 |
| 2010/0145411 A1 | 6/2010 | Spitzer |
| 2010/0161000 A1 | 6/2010 | Litvak et al. |
| 2010/0202625 A1 | 8/2010 | Boretzki et al. |
| 2010/0296679 A1 | 11/2010 | Hofmann et al. |
| 2011/0064241 A1 | 3/2011 | Kulkarni |
| 2011/0077698 A1 | 3/2011 | Tsampazis et al. |
| 2011/0106209 A1 | 5/2011 | Saoji |
| 2011/0235814 A1* | 9/2011 | Van Den Heuvel ... H04R 25/70 381/60 |
| 2011/0238176 A1 | 9/2011 | Bradley et al. |
| 2012/0109006 A1* | 5/2012 | James ................ A61N 1/37247 600/559 |
| 2012/0219159 A1 | 8/2012 | Burk et al. |
| 2013/0114836 A1 | 5/2013 | Fichtl et al. |
| 2014/0086439 A1 | 3/2014 | Johnston et al. |
| 2014/0114375 A1 | 4/2014 | Chapa et al. |
| 2015/0335890 A1 | 11/2015 | Fredelake et al. |

FOREIGN PATENT DOCUMENTS

| | | |
|---|---|---|
| WO | WO-97/38653 | 10/1997 |
| WO | WO-2001/026419 | 4/2001 |
| WO | WO-2008/092183 | 8/2008 |
| WO | WO-2010/031880 | 3/2010 |
| WO | WO-2011/032021 | 3/2011 |
| WO | WO-2011/051831 | 5/2011 |
| WO | WO-2012/056427 | 5/2012 |
| WO | WO-2012/161717 | 11/2012 |
| WO | WO-2012/166108 | 12/2012 |
| WO | WO-2014/108201 | 7/2014 |
| WO | WO-2016/004970 | 1/2016 |
| WO | WO-2016/024978 | 2/2016 |

OTHER PUBLICATIONS

Non-Final Office Action received in U.S. Appl. No. 14/760,465 dated May 3, 2016.

Final Office Action received in U.S. Appl. No. 14/760,465 dated Sep. 7, 2016.

International Search Report and Written Opinion received in International Application No. PCT/US2014/064436, dated Nov. 20, 2014.

* cited by examiner

SYSTEM FOR COMBINED NEURAL AND ACOUSTIC HEARING STIMULATION

The invention relates to a hearing assistance system comprising an auditory prosthesis for neural stimulation, such as cochlear implant device, and a hearing aid.

Cochlear implants are the standard of care for patients with severe to profound hearing loss; cochlear implants stimulate the auditory nerve, typically by an electrode array, thereby electrically bypassing the non-functioning hair-cells. Due to the success of cochlear implants, the indication range is moving towards residual acoustic hearing. It is known that in such cases the hearing performance can be improved by adding acoustic stimulation to the electrical stimulation, typically, in the low frequency range below 1.5 kHz.

Systems for bimodal stimulation of the hearing comprise a cochlear implant at the ipsilateral ear and a device for acoustic stimulation of the ipsilateral ear or the contralateral ear. Systems with electric and acoustic stimulation of the same ear are also known as hybrid devices or EAS devices. In systems with contralateral acoustic stimulation the acoustic stimulation device typically is an (electro-acoustic) hearing aid.

In a cochlear implant (CI) a frequency allocation map specifies which frequency sub-ranges (frequency band) of the input audio signal (i.e. the audio signal provided by the microphone and/or an external audio source) are assigned to each stimulation channel, with the stimulation channels being formed by the implant electrodes. Over time, a CI patient adapts to his specific frequency allocation. For example, a need to modify the frequency allocation of the CI may occur in cases in which a patient first is provided with a CI with electrical stimulation only and later is provided in addition with acoustic stimulation of the same ear (EAS system).

Usually, the lower input signal frequencies are selected for acoustic stimulation, while the remaining higher input signal frequencies are selected for electrical stimulation.

Typically, when implementing such bimodal stimulation system, after implantation of the electrical part of the device, electric stimulation is applied alone, i.e. without acoustic stimulation for a certain period in order to enable the patient to get used to the new "electric" hearing impression before acoustic stimulation is activated. Often, the patients need a certain acclimatization period to get used to the new "combined" stimulation hearing impression until the audiologically prescribed acoustic amplification (e.g. described by a fitting formula like DSL-I/O, NAL-RP, etc.) can be applied, so that often several fitting appointments at the implantation clinic may be required, causing additional effort for the clinic as well as for the patient. Typically, such acclimatization period have a duration of a few weeks or months.

In case that such repeated fitting of the acoustic stimulation during the acclimatization period is omitted, the patient could become "underfitted" regarding acoustic stimulation, which may result in suboptimal hearing performance and sound quality.

U.S. Pat. No. 8,571,674 B2 relates to an iterative fitting method for a multimodal hearing assistant system including electrical and acoustic stimulation.

US 2005/0261748 A1 relates to a fitting method for a hybrid device used by a patient having residual acoustic hearing capability at the ipsilateral ear, wherein the portion of the cochlea having residual acoustic hearing capability is determined by measuring the neural response to acoustic and/or electrical stimulation.

US 2011/0238176 A1 likewise relates to a fitting method for a hybrid device, wherein a tonotopic response for the residual hearing of the ipsilateral cochlear is measured to obtain a place-frequency map.

U.S. Pat. No. 8,155,747 B2 relates to a method of fitting a bilateral hearing system comprising a CI device at one ear and a hearing aid at the other ear.

U.S. Pat. No. 8,565,889 B2 relates to a method of adjusting the fitting parameters of a CI/EAS device or a digital hearing aid based on patient feedback in order to implement an interactive fitting process.

WO 2012/056427 A2 relates to a fitting method for a bimodal system, wherein the cut-off frequency separating the acoustic stimulation range from the electric stimulation range is selected automatically and potentials evoked by the electrical stimulation may be recorded at the time of fitting of the device, or recorded and stored automatically every time the sound processor is placed on the head, so that hearing can be monitored for changes on a daily basis and these changes are compensated for.

It is an object of the invention to provide for a bimodal hearing assistance system which allows for optimal hearing performance and sound quality and which requires nevertheless only little fitting efforts.

According to the invention, this object is achieved by a hearing assistance system as defined in claim 1 and a stimulation method as defined in claim 32, respectively.

The invention is beneficial in that, by controlling the audio signal processing unit of the hearing aid such that, during an adjustment period, the value of at least one parameter used in the processing of the audio signal is automatically changed from a first value to a second value as a function of the time having passed since a reference point in time, an automatic acclimatization of the fitting of the hearing aid is implemented, so that after the acclimatization period optimal fitting of the acoustic signal processing can be achieved without the need for repeated fitting sessions, thereby reducing the efforts required for the clinic and the patient.

Preferably, the at least one parameter is changed, during the adjustment period, as a monotonous function of time, with the value of the parameter remaining at the second value after the adjustment period. In particular, the second value may be a target value corresponding to a final fitting prescription of the hearing assistance system. Typical durations of the adjustment period are from one day to one year.

Typically, the reference point in time is the point in time of the first activation of the hearing aid.

Typically, the at least one automatically adjustable parameter is an audio signal amplification parameter, such as the gain to be applied to the input signal as a function of frequency and input signal level, with the gain usually increasing as a function of time during the adjustment period. Further, the at least one automatically adjustable parameter may be a compression ratio of a dynamic compression applied to the input signal, with the compression ratio typically being progressively reduced as a function of time during the adjustment period.

According to another example, the at least one automatically adjustable parameter is an upper-cut off frequency of the processed audio signal, with the value of the upper cut-off frequency typically being increased during the adjustment period in order to gradually expand the frequency range of acoustic stimulation during the adjustment period.

Preferably, the auditory prosthesis and the hearing aid are coupled in a manner so as to synchronize the change of at least one parameter used in the generation of the neural stimulation signal with the automatic change of the at least one automatically adjustable parameter used in the processing of the input audio signal.

According to one embodiment, the auditory prosthesis and the hearing aid are integrated within a hybrid device to be worn at one of the user's ears, i.e. the auditory prosthesis and the hearing aid together form an EAS device.

The term "hearing aid" as used herein is to be understood in a functional manner for acoustic hearing stimulation, i.e. the "hearing aid" may be physically implemented as part of, or integrated with, the auditory prosthesis (i.e. in order to implement a hybrid EAS device), or it may be physically implemented as a separate device (e.g. worn at the other ear, in order to implement a bimodal system for electric stimulation of one ear and acoustic stimulation of the other ear).

Preferred embodiments of the invention are defined in the dependent claims.

Hereinafter, examples of the invention will be illustrated by reference to the attached drawings, wherein:

FIG. 8 is an illustration of the acclimatization of the acoustic amplification, wherein the output level is shown as a function of the input level for different points in time during the adjustment period;

Figure 1:
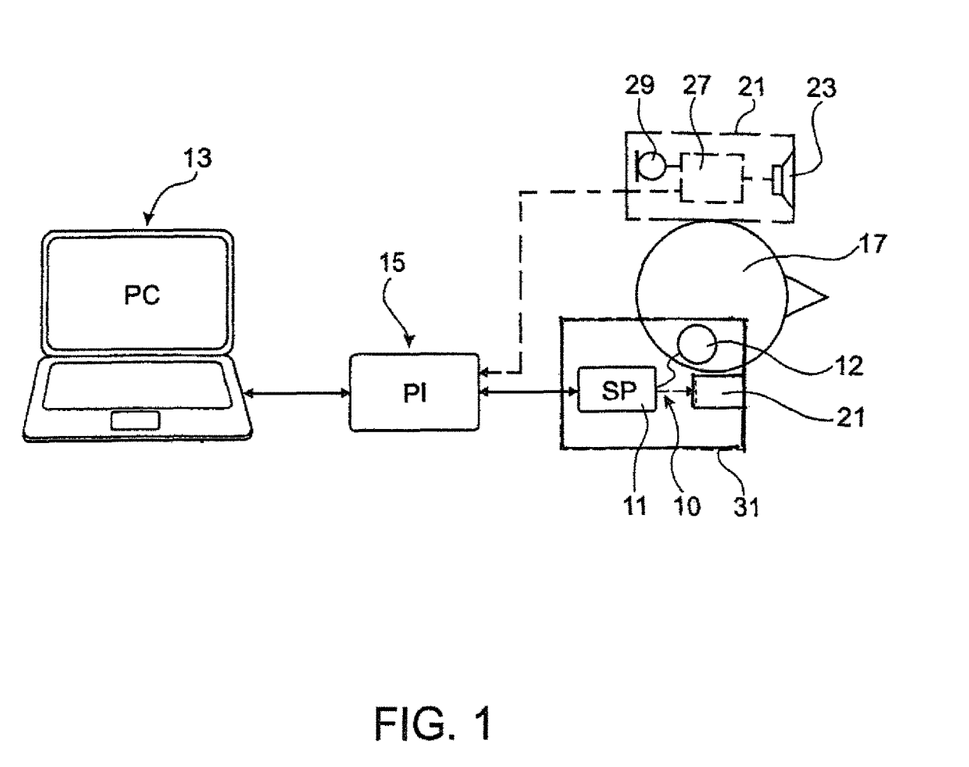
FIG. 1 is a schematic representation of an example of a system according to the invention.

FIG. 1 is a schematic representation of an example of a bimodal stimulation system according to the invention, comprising a CI device 10 worn by a patient 17 at the ipsilateral ear and including a sound processing subsystem 11 and an implantable stimulation subsystem 12. The stimulation system also comprises a hearing aid 21 for additional acoustic stimulation of the patient's hearing, which may be integrated within the CI device 10 in order to stimulate the ipsilateral ear (thereby forming, together with the CI device 10, an EAS system 31) or which may be provided separately at the contralateral ear in order to stimulate the contralateral ear (the latter variant is shown in dashed lines in FIG. 1). The hearing aid 21 comprises a microphone arrangement 29 for capturing audio signals from ambient sound (or may use a microphone 20 of the CI device), an audio signal processing unit 27 for processing the captured audio signals, and the loudspeaker 23 to which the processed audio signals are supplied.

In the example of FIG. 1 also a fitting/programming unit 13, which may be implemented as a computer, and a programming interface 15 are shown. The programming unit 13 communicates with the sound processing subsystem 11 via the programming interface 15, which may be implemented as a wired or wireless connection. It is to be understood that the programming unit 13 is used with the bimodal system only for adjustment/fitting, but not during normal operation of the bimodal system.

Figure 5:
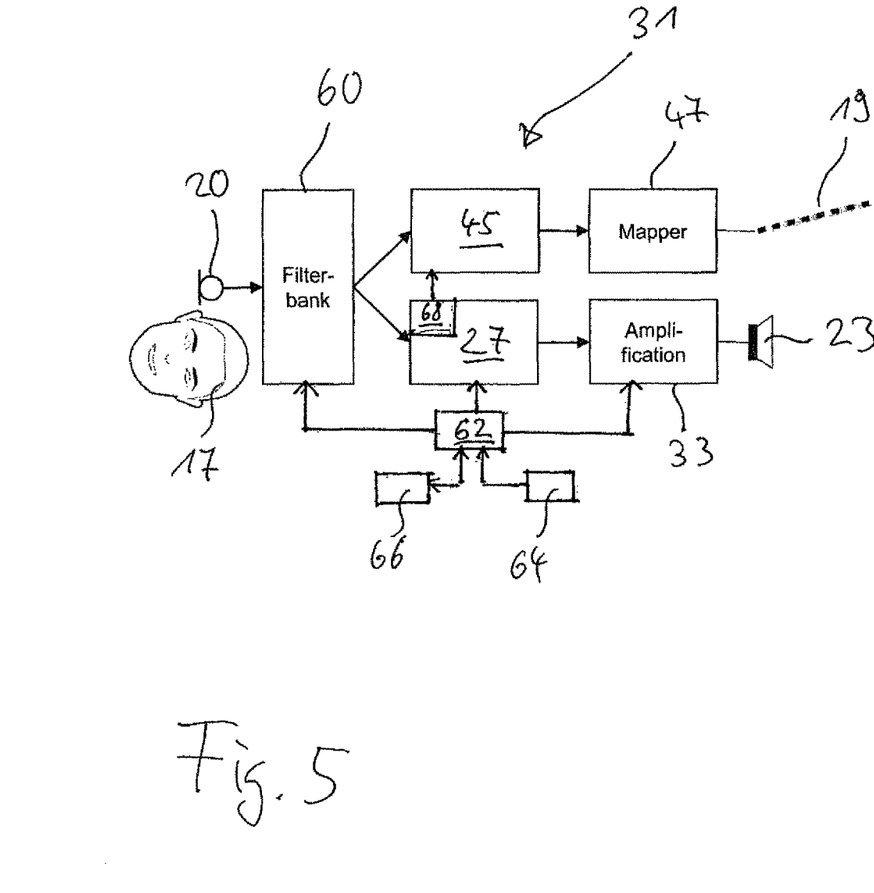
FIG. 5 is a block diagram of an example of the signal processing structure of an EAS system according to the invention.

FIG. 5 is a schematic block diagram of the signal processing in the EAS system 31 of FIG. 1, comprising at least one microphone 20 for capturing an input audio signal, a filter bank 60 for splitting the captured input audio signal into a plurality of frequency bands, an audio signal processing unit/block 27, an amplifier 33 for amplifying the audio signals processed by the audio signal processing unit 27, a loudspeaker 23 for generating sound according to the amplified processed audio signals, a block 45 for generating neural stimulation signals from the input audio signal, a "mapper block" 47 for mapping the stimulation signal onto the stimulation channels, and an electrode array 19. The elements 27, 33 and 23 are functionally attributed to the hearing aid 21, and the elements 45, 47 and 19 are functionally attributed to the CI device 10. It is to be understood that the signal processing required for the acoustic stimulation and the electric stimulation, while illustrated in separate blocks in FIG. 5, in practice may be implemented, at least in part, in a common block/unit, such as in the sound processor 24, i.e. the audio signal processing unit 27 may be physically implemented as part of the sound processor 24.

The signal processing of the CI device 10 now will be explained in more detail by reference to FIGS. 2 to 4.

Figure 2:
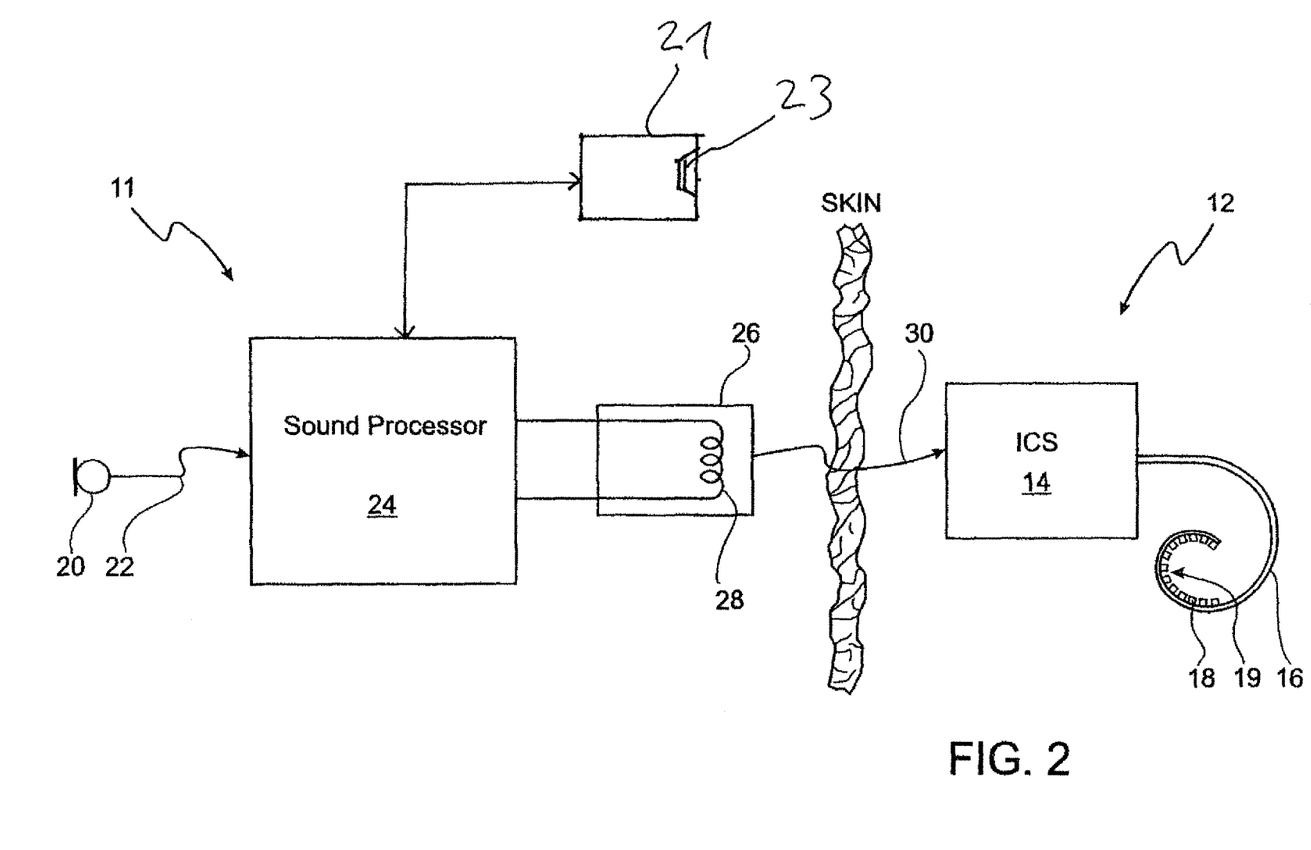
FIG. 2 is a schematic representation of an example of the CI device of the system of FIG. 1.

In FIG. 2 an example of the cochlear implant device 10 of the system of FIG. 1 is shown schematically. The sound processing sub-system 11 serves to detect or sense an audio signal and divide the audio signal into a plurality of analysis channels, each containing a frequency domain signal (or simply "signal") representative of a distinct frequency portion of the audio signal. A signal level value and optionally a noise level value are determined for each analysis channel by analyzing the respective frequency domain signal, and a noise reduction gain parameter may be determined for each analysis channel as a function of the signal level value and the noise level value of the respective analysis channel. Noise reduction may be applied to the frequency domain signal according to the noise reduction gain parameters to generate a noise reduced frequency domain signal. Stimulation parameters are generated based on the noise reduced frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlea of a patient 17 in accordance with the stimulation parameters received from the sound processing sub-system 11. Electrical stimulation is provided to the patient 17 via a CI stimulation assembly 18 comprising a plurality of stimulation channels, wherein various known stimulation strategies, such as current steering stimulation or N-of-M stimulation, may be utilized.

The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp-on time, and ramp-off time of the stimulation current that is applied to the stimulation site.

Figure 3:
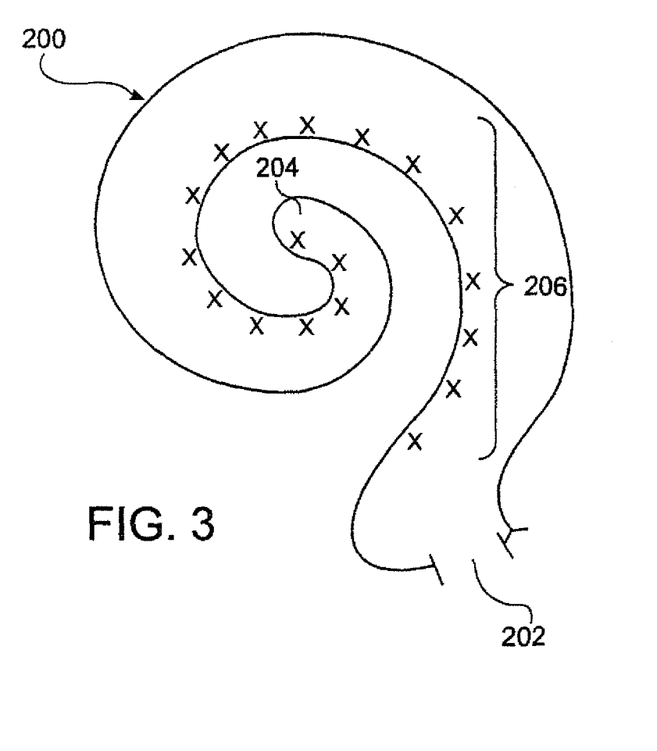
FIG. 3 is a schematic cross-sectional view of a human cochlea with marked stimulation sites.

FIG. 3 illustrates a schematic structure of the human cochlea 200. As shown in FIG. 3, the cochlea 200 is in the shape of a spiral beginning at a base 202 and ending at an apex 204. Within the cochlea 200 resides auditory nerve tissue 206 which is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply stimulation to different locations within the cochlea 200 (e.g., different locations along the auditory nerve tissue 206) to provide a sensation of hearing.

Returning to FIG. 2, sound processing subsystem 11 and stimulation subsystem 12 is configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application. In particular, the control parameters may include a frequency allocation table (FAT) which determines the respective frequency range allocated to a certain electrode.

In the example shown in FIG. 2, the stimulation subsystem 12 comprises an implantable cochlear stimulator (ICS) 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 2, the sound processing sub-system 11 is designed as being located external to the patient 17; however, in alternative examples, at least one of the components of the sub-system 11 may be implantable.

In the example shown in FIG. 2, the sound processing sub-system 11 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor (PSP). In the example of FIG. 2 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

Figure 4:
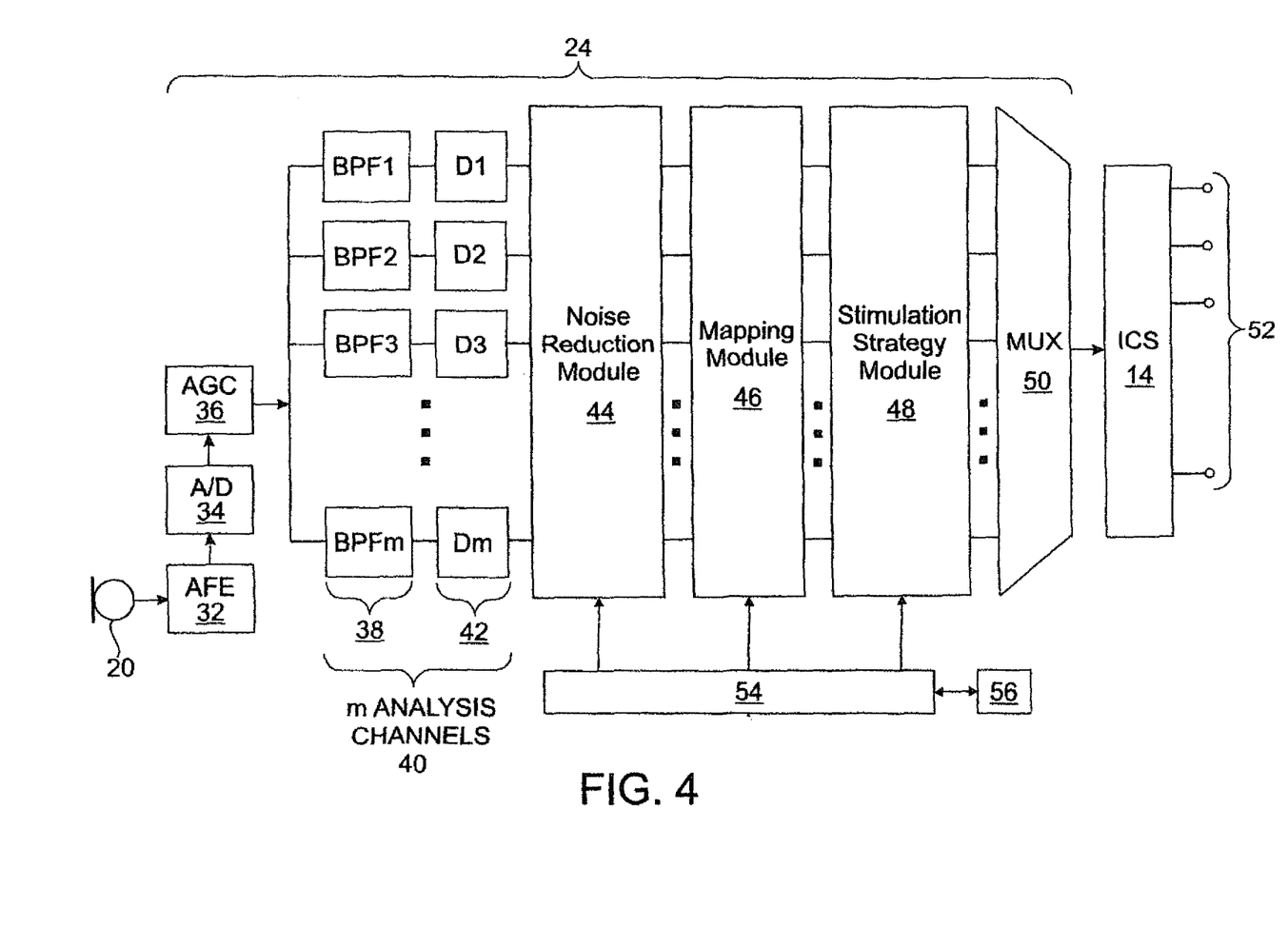
FIG. 4 is a block diagram of an example of the signal processing structure of a CI device to be used with the invention.

In FIG. 4 a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filterbank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then distribute the resulting frequency bins across the analysis channels 40.

The signals within each analysis channel 40 are input into an envelope detector 42 in order to determine the amount of energy contained within each of the signals within the analysis channels 40 and to estimate the noise within each channel. After envelope detection the signals within the analysis channels 40 may be input into a noise reduction module 44, wherein the signals are treated in a manner so as to reduce noise in the signal in order to enhance, for example, the intelligibility of speech by the patient.

The optionally noise reduced signals are supplied to a mapping module 46 which serves to map the signals in the analysis channels 40 to the stimulation channels S1 . . . Sn. For example, signal levels of the noise reduced signals may be mapped to amplitude values used to define the electrical stimulation pulses that are applied to the patient 17 by the ICS 14 via M stimulation channels 52. For example, each of the m stimulation channels 52 may be associated to one of the stimulation contacts 19 or to a group of the stimulation contacts 19.

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels S1 . . . Sn in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

The sound processor 24 may operate in accordance with at least one control parameter which is set by a control unit 54. Such control parameters, which may be stored in a memory 56, may be the most comfortable listening current levels (MCL), also referred to as "M levels", threshold current levels (also referred to as "T levels"), dynamic range parameters, channel acoustic gain parameters, front and back end dynamic range parameters, current steering parameters, amplitude values, pulse rate values, pulse width values, polarity values, the respective frequency range assigned to each electrode and/or filter characteristics. Examples of such auditory prosthesis devices, as described so far, can be found, for example, in WO 2011/032021 A1.

Figure 6:
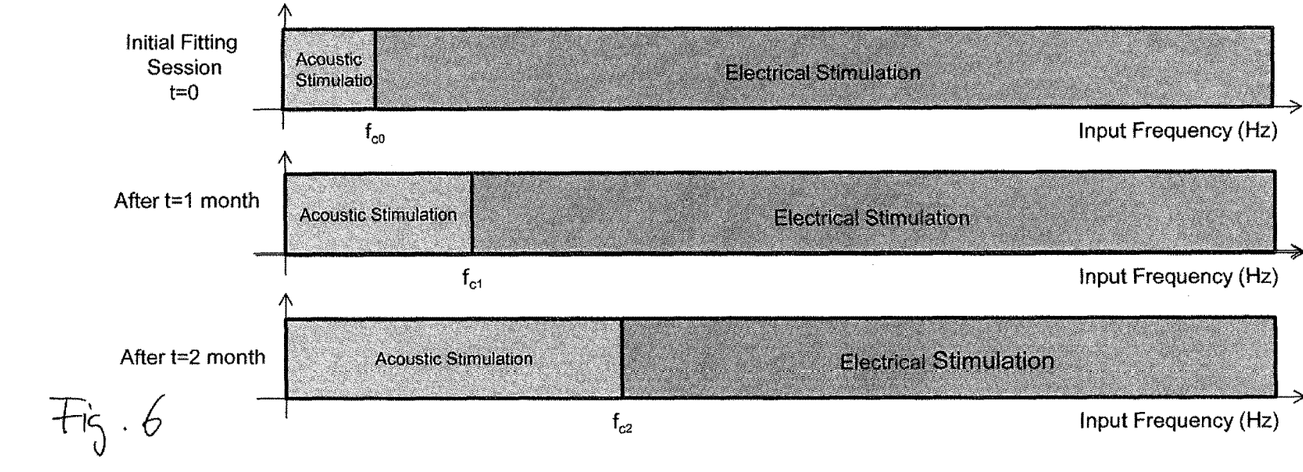
FIG. 6 is a schematic illustration of the acclimatization of the bandwidth of the acoustic stimulation and the crossover frequency.

According to one example, the frequencies of the input audio signal are divided by a crossover frequency $f_c$ into a lower frequency range below the crossover frequency which is supplied to the hearing aid 21 for acoustic stimulation and an upper frequency range above the crossover frequency which is supplied to the CI device for electric stimulation, see as also illustrated in FIG. 6. However, rather than separating the frequencies of the input audio signal into an acoustic stimulation range and an electric stimulation range, there could be overlapping acoustic and electric stimulation; for example, part of or the entire input signal frequency range could be stimulated both acoustically and electrically.

The EAS system 31 also comprises a control unit 62 for controlling the audio signal processing unit 27 and the filter bank 60 in such a manner that at least one parameter used in the processing of the input audio signal is controlled such that the value of this parameter is automatically changed from a first value to a second value as a function of the time having passed since a reference point in time. To this end, the system 31 comprises an internal clock 64 and a non-volatile memory 66 for storing the instantaneous values of the at least one automatically adjustable parameter.

Typically, the automatically adjustable parameter is automatically changed from the first value to the second value as a monotonous function of the time having passed since the reference point in time. For example, the parameter may be changed according to a linear or an asymptotic increase from the first value to the second value. Typically, the value of the automatically adjustable parameter remains at the second value after the adjustment period, with the first value representing an initial value and the second value representing a final value. For example, the second value may be a target value, corresponding to a final prescription of the hearing aid 21, such as prescribed by a fitting formula like DSL-I/O or NAL-RP.

Typically, the reference point in time is the point in time of the first activation of the hearing aid 21, which typically occurs in a first fitting session for adjusting the hearing aid (the hearing aid may be fitted/activated together with the fitting of the CI device, or it may be fitted/activated some time, for example a few weeks or months, after implantation/activation of the CI device in order to allow the patient's hearing to get accustomed to the electric stimulation prior to fitting of the hearing aid). Typically, during such first fitting session for the hearing aid, a basic acoustic amplification scheme may be programmed which comprises gain levels significantly lower than an audiological fitting formula width require and/or comprising an acoustic bandwidth which is lower than the audiological target bandwidth. Further, the audiologist may set target values of such amplification/bandwidth parameters which are to be automatically approached by the hearing aid 21 in the course of the adjustment period. Also the required time constant for such automatic adjustment/adaptation, i.e. the length of the respective adjustment period for each parameter, may be set by the audiologist in the fitting session. In particular, different time constants/adjustment period lengths may be set for different parameters. Depending on the respective parameter, typical adjustment period lengths may be several weeks or months.

As already mentioned above, the filter bank 60 and the audio signal processing unit 27 may be controlled by the control unit 62 in such a manner that acoustic stimulation is applied only in a low frequency range of the input audio signal below a crossover frequency acting as an upper-cut off frequency of an acoustic stimulation frequency range, whereas electric stimulation is applied only in a high frequency range above the crossover frequency (this also requires corresponding control action in the signal processing blocks 45 and 47 of the CI device 10).

The audio signal processing in the audio signal processing unit 27 may include compression of frequencies in the input audio signal in a range from the crossover frequency to an upper compression limit into a frequency range below the crossover frequency.

Typically, the crossover frequency may be set to a relatively low initial value $f_{c0}$ in the initial fitting session and then may be automatically increased during the adjustment period until a final value is reached at the end of the adjustment period. This is illustrated in FIG. 6, where the initial value is labeled "$f_{c0}$", an intermediate value set after one month is labeled "$f_{c1}$", and the final value set after two months is labeled "$f_{c2}$".

Figure 7:
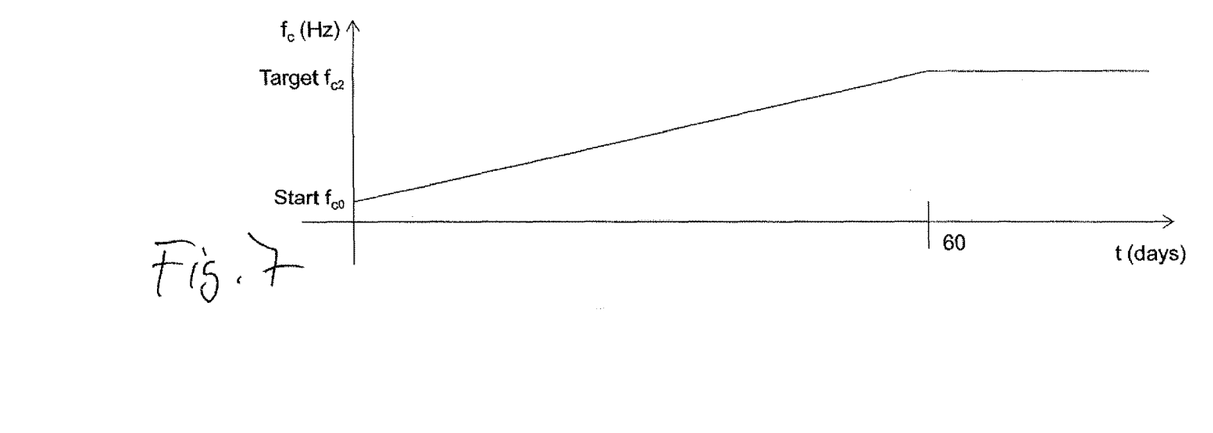
FIG. 7 is an example of the value of the crossover frequency as a function of time during an adjustment period.

In FIG. 7 an example of the value of the crossover frequency $f_c$ as a function of time is shown, according to which the value is increased according to a monotonous (for example, linear) function until the target value $f_{c2}$ is reached after two months.

Similarly, in case of frequency compression of frequencies above the crossover frequency into the acoustic frequency range the upper limit of the compression may be continuously increased during the adjustment period (such increase of the width of the frequency compression range may be applied also in case in which the crossover frequency is not changed during the adjustment period).

Figure 9:
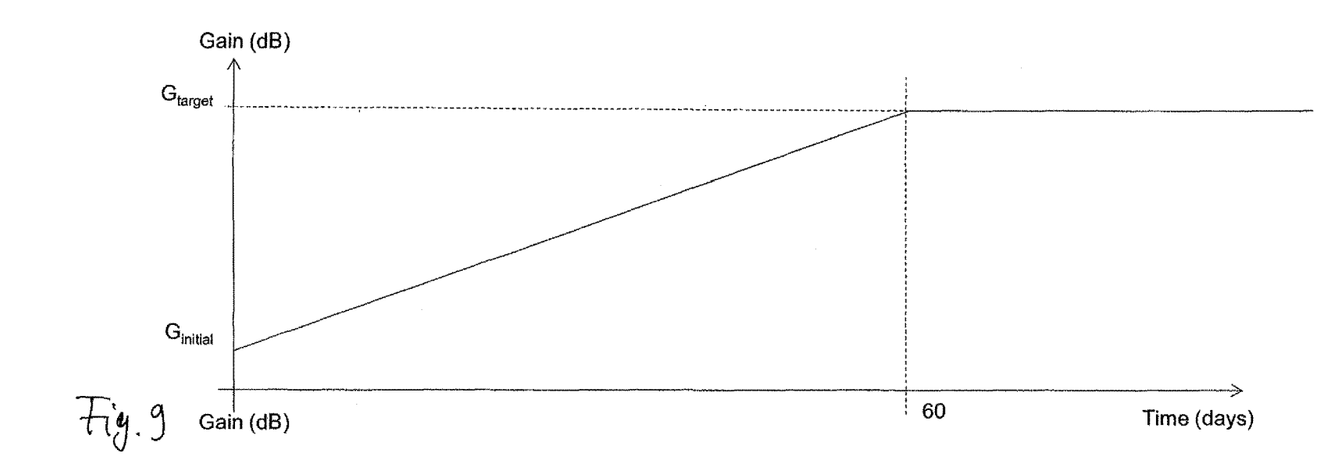
FIG. 9 is an example of the acoustic gain as a function of time during the adjustment period.
Figure 10:
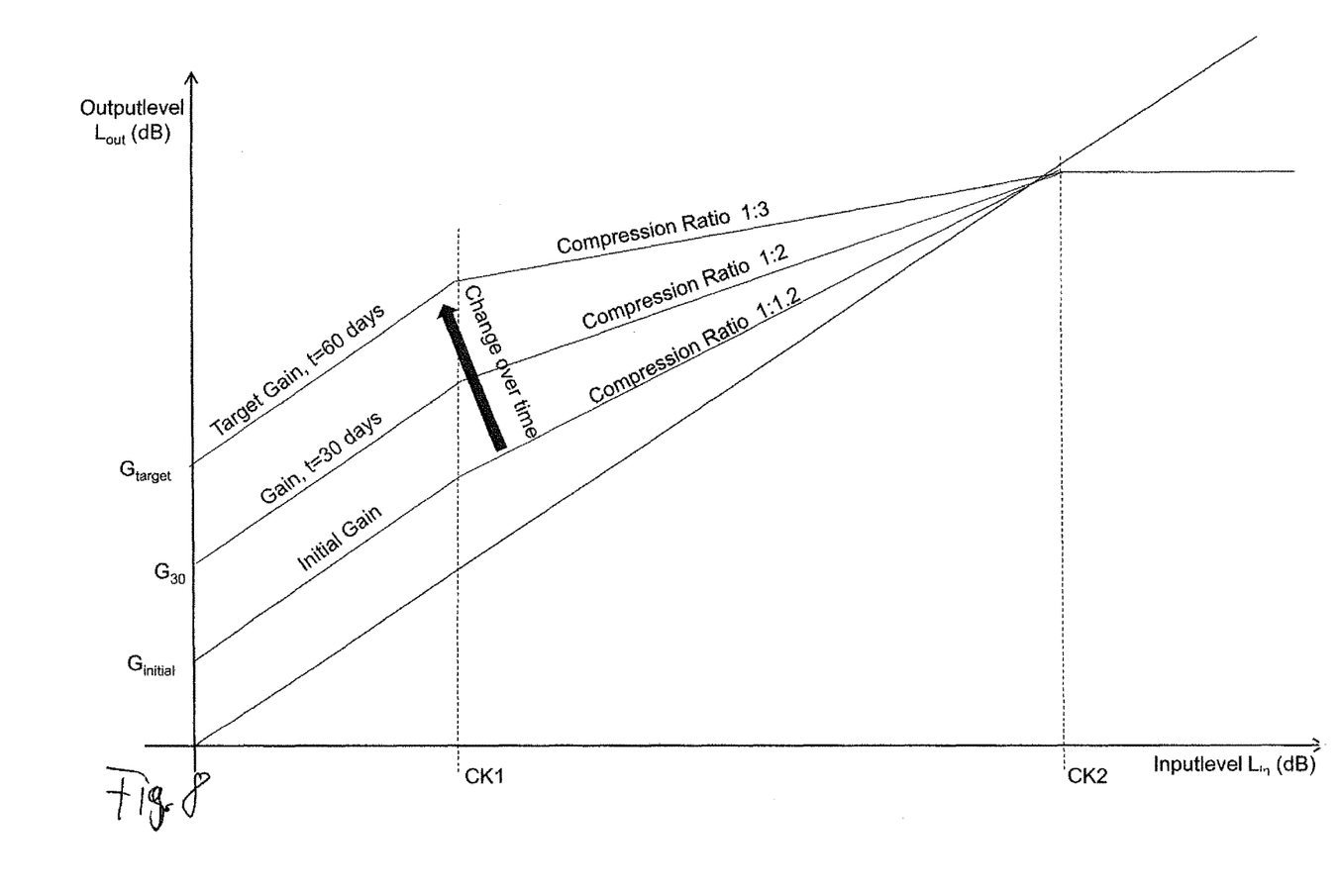
FIG. 10 is an example of the compression ratio as a function of time during the adjustment period.

As illustrated in FIGS. 8 to 10, the gain to be applied the input signal as a function of frequency and input signal level may be automatically adjusted during an adjustment (practically, a certain gain value is applied to the input signal in each frequency band of the filter bank 60). Typically, the gain increases for all frequency bands processed by the hearing aid 21 as a function of time during the adjustment period. However, the relative increase may be different for different frequency ranges; for example, the gain applied at higher frequencies may increase relative to the gain applied at lower frequencies, i.e. the gain increase at higher frequencies may be more pronounced than the gain increase at lower frequencies.

An example of the automatic gain increase during the adjustment period is shown in FIG. 9, wherein the gain applied to a certain frequency band increases from an initial value $G_{initial}$ monotonously until a target gain value $G_{target}$ is reached at the end of the adjustment period (in the example of FIG. 9, such gain increase is a linear function of time).

Usually, the gain applied to the audio signal is not only a function of the frequency, but also of the input signal level. This is illustrated in FIG. 8 wherein the output level of the processed audio signal is shown as a function of the level $L_{in}$ of the input signal. According to the example of FIG. 8 the gain is constant at low input signal levels, up to a knee point CK1. At intermediate input signal levels in a range from CK1 to CK2 dynamic compression is applied to the input signal in order to compress the input signal at a certain compression ratio i.e. in the input level range the gain decreases with increasing input signal level. At high input signal levels above a value CK2 the output level is kept constant.

The diagram of FIG. 8 shows three gain curves, namely an initial gain curve, a gain curve to be applied after thirty days of the adjustment period and a third gain curve to be applied after sixty days of the adjustment period, with the latter curve corresponding to the target gain curve to be retained after the adjustment period. In the low input level range below CK1 the monotonous gain increase illustrated in FIG. 9 can be seen, whereas in the intermediate input level range between CK1 and CK2 it can be seen that the compression ratio is gradually decreased as a function of time, namely from initial value of 1:1.2 to 1:2 at thirty days and to 1:3 at sixty days.

Such decrease of the compression ratio as a function of the time having passed since at the beginning of the adjustment period is illustrated in FIG. 10.

According to another example, the automatically adjustable parameters may include the strength of a noise reduction applied to the input audio signal processing unit, with the noise reduction strength increasing during the adjustment period, starting from soft settings. Preferably, there is a corresponding co-adaptation of the noise reduction strength in the electric stimulation signal.

The EAS system 31 may comprise a classifier unit (indicated at 68 in FIG. 5) for determining the present auditory scenes by analyzing the input audio signal in order to adapt the audio signal processing in the hearing aid 21 and the stimulation signal generation in the CI device 10 to the presently prevailing acoustic environment, as is known in the art. While a classifier usually is used for selecting the most appropriate audio signal processing program, the output of such classifier unit 68 also may be used for selecting time constants used in the automatic parameter adjustment during the adjustment period according to the detected acoustic environment; in particular, the duration of the adjustment period may depend on the auditory scenes as determined by the classifier unit (or, more precisely, on the history of the auditory scenes during the adjustment period). For example, the duration of the adjustment period may be shorter for auditory scenes with high (frequency-averaged) input signal levels relative to auditory scenes with low (frequency-averaged) input signal levels. In other words, quiet or soft speech contributes less to the acclimatization process (resulting in the need for a longer adjustment period) than speech-in-noise situations or any loud sounds (resulting in faster acclimatization i.e. allowing a shorter adjustment period).

According to a further example, the acclimatization functions (i.e. which parameters are to be selected and how these parameters are to be changed during the adjustment period) may be selected according to the auditory scene as detected by the classifier unit. In this case, an audio signal processing program is selected according to the determined auditory scene, and the related acclimatization parameters are adjusted; in particular, different acclimatization parameters may be selected for different audio signal programs and/or the manner of how the parameter is changed as a function of time during the acclimatization period may be different for different audio signal processing programs.

Usually, the electrical stimulation parameters, i.e. parameters used in the generation of the electric stimulation signal, are automatically co-adapted to the automatic adjustment of the audio signal processing parameters of the acoustic stimulation during the adjustment period. To this end, the CI device 10 is coupled to the hearing aid 21 in a manner so as to synchronize an automatic adjustment of parameters used in the generation of the electric stimulation signal with the automatic adjustment of parameters of the audio signal processing during the adjustment period (in other words, the electric and acoustic signal processing is to be synchronized, which may require appropriate actual data exchange between the CI signal processing facility and the audio signal processing facility in case that these facilities are implemented separately from each other; in case that the CI signal processing and the audio signal processing are implemented in the same facility, no actual data exchange would be required).

In particular, the increase of the bandwidth of the acoustic stimulation during the adjustment period, with the crossover frequency increasing during the adjustment period, as shown for example in FIGS. 6 and 7, may result in a corresponding reduction of the bandwidth of the electrical stimulation, as illustrated in FIG. 6, i.e. the lower limit of the frequencies of the input signal mapped to the stimulation electrodes is increased in the course of the adjustment period in conformity with the increase of the crossover frequency (corresponding to the upper limit of the acoustic stimulation). Consequently, the mapping scheme applied in the electric stimulation is adjusted according to the increase of the crossover frequency; in particular, frequencies below the crossover frequency will not be assigned to a stimulation channel.

However, as already mentioned above, there may be some or full overlap of acoustic and electric stimulation, so that the upper cut-off frequency of the audio signal processing does not necessarily equal the lower cut-off frequency of electric stimulation.

According to another example, not only the mapping scheme may be co-adapted in synchronism with the automatic adjustment of the audio signal processing parameters, but also the levels of the electric stimulation may be co-adapted to changes of parameters in the audio signal processing. For example, the level of the electric stimulation signal may be reduced in synchronism with an increase of an audio signal amplification parameter during the adjustment period. In particular, electric stimulation signal levels may be reduced in a low frequency arrange relative to the electric stimulation levels in a high frequency range (acoustic stimulation occurs primarily at low frequencies, so that the low frequency electric stimulation is affected more by the acoustic stimulation than the electric stimulation at high frequencies).

In case of a bilateral fitting of the patient with an EAS system the acclimatization process in the right ear system and the left ear system should be synchronized by respective communication between the two systems, such as by a binaural wireless link.

It is to be understood that the present invention may be applied to EAS systems but also to bimodal systems wherein electric stimulation is applied to one ear while acoustic stimulation is applied to the other ear (as indicated by dashed lines in FIG. 1).

It is also to be understood that the neural hearing stimulation need not necessarily occur by electric stimulation via electrodes implanted within the cochlea; rather, neural stimulation also could occur e.g. by light or heat stimuli applied within the cochlea, as is known in the art.

The invention claimed is:

1. A hearing assistance system comprising an auditory prosthesis device for neural stimulation of a patient's hearing at one of the patient's ears and a hearing aid for acoustic stimulation of the patient's hearing at the same one or the other one of the patient's ears, the system including providing means for providing an input audio signal;

the auditory prosthesis device comprising:

a sound processor for generating a neural stimulation signal from at least part of the input audio signal, and an implantable stimulation assembly for stimulation of the patient's hearing according to the neural stimulation signal;

the hearing aid comprising:
an audio signal processing unit for processing at least part of the input audio signal,
an acoustic output transducer for stimulating the patient's hearing according to the processed audio signals, and
a control unit for controlling the audio signal processing unit, the control unit being adapted to control at least one parameter used in the processing of the input audio signal such that, during an adjustment period, the value of the at least one parameter is automatically changed from a first value to a second value as a function of time having passed since a reference point in time;

wherein the auditory prosthesis is adapted to communicate with the hearing aid in a manner so as to synchronize a change of at least one parameter used in the generation of the neural stimulation signal with a change of said at least one parameter used in the processing of the input audio signal.

2. The system of claim 1, wherein during the adjustment period the parameter value is automatically changed from the first value to the second value as a monotonous function of the time having passed since the reference point in time.

3. The system of claim 2, wherein the automatic change of the parameter value during the adjustment period is a linear or asymptotic increase from the first value to the second value.

4. The system of claim 1, wherein after the adjustment period the value of the parameter remains at the second value.

5. The system of claim 4, wherein the second value is a target value corresponding to a final fitting prescription of the hearing assistance system.

6. The system of claim 1, wherein a duration of the adjustment period is different for different ones of the at least one parameter.

7. The system of claim 1, wherein a duration of the adjustment period is from one day to 12 months.

8. The system of claim 1, further comprising a classifier unit for determining a present auditory scene by analyzing the input audio signal.

9. The system of claim 8, wherein a duration of the adjustment period depends on the present auditory scene as determined by the classifier unit during the adjustment period.

10. The system of claim 9, wherein the duration of the adjustment period is shorter for auditory scenes with high frequency-averaged input signal levels relative to auditory scenes with low frequency-averaged input signal levels.

11. The system of claim 8, wherein the control unit is adapted to select an audio signal processing program of the audio signal processing unit according to the determined present auditory scene, wherein different ones of the at least one parameter are selected for different audio signal processing programs and/or a manner of how the at least one parameter is changed as a function of the time having passed since the reference point in time is different for different audio signal processing programs.

12. The system of claim 1, wherein the reference point in time is a point in time of the first activation of the hearing aid.

13. The system of claim 1, wherein the at least one parameter comprises an audio signal amplification parameter.

14. The system of claim 13, wherein the at least one parameter comprises the gain to be applied to the input signal as a function of frequency and input signal level.

15. The system of claim 14, wherein the system comprises divider means for dividing the input signal into a plurality of frequency bands, and wherein the at least one parameter comprises the gain to be applied to the input signal in each frequency band.

16. The system of claim 15, wherein the gain applied at higher frequencies increases relative to the gain applied at lower frequencies during the adjustment period.

17. The system of claim 14, wherein during the adjustment period the gain increases as a function of time.

18. The system of claim 14, wherein the gain to be applied to the input signal is reduced with increasing input signal level in a manner so as to apply dynamic compression to the input signal at a compression ratio, wherein the at least one parameter comprises the compression ratio, with the compression ratio being progressively reduced as function of time during the adjustment period.

19. The system of claim 18, wherein the dynamic compression is applied only for input signal levels above a compression threshold value.

20. The system of claim 1, wherein the at least one parameter comprises a strength of a noise reduction applied in the audio signal processing unit, and wherein the strength increases during the adjustment period.

21. The system of claim 1, wherein the processed audio signal has an upper cut-off frequency in order to avoid acoustic stimulation above the cut-off frequency, wherein the at least one parameter comprises the upper cut-off frequency, and wherein a value of the upper cut-off frequency increases during the adjustment period.

22. The system of claim 21, wherein the audio signal processing includes a frequency compression of frequencies in the input audio signal above the cut-off frequency up to an upper compression frequency limit to frequencies below the cut-off frequency, and wherein the upper compression frequency limit increases during the adjustment period.

23. The system of claim 1, wherein the system comprises dividing means for dividing the input audio signal into a plurality of analysis channels, each containing a frequency domain signal representative of a distinct frequency portion of the audio signal, determining means for determining a signal level for each analysis channel by analyzing the respective frequency domain signal, signal generating means for generating a neural stimulation signal for each analysis channel according to the respective signal level, and a mapping unit for allocating the analysis channels to stimulation channels according to an adjustable mapping scheme, wherein analysis channels having a center frequency below a crossover frequency are not allocated to a stimulation channel.

24. The system of claim 23, wherein the mapping scheme is adjusted in response to changes of an upper cut-off frequency of the audio signal processing.

25. The system of claim 24, wherein the sound processor is adapted to change the crossover frequency in synchronism with the changes of the upper cut-off frequency.

26. The system of claim 25, wherein the crossover frequency equals or is fixedly coupled with the upper cut-off frequency of the audio signal processing.

27. The system of claim 1, wherein the at least one parameter comprises a level of the neural stimulation signal, wherein the level of the neural stimulation signal is reduced in synchronism with an increase of an audio signal amplification parameter during the adjustment period of the hearing aid.

28. The system of claim 27, wherein said level of the neural stimulation signal is a level of a low frequency range of the neural stimulation signal, with said level of said low frequency range being reduced relative to a level of a high frequency range of the neural stimulation signal.

29. The system of claim 1, wherein the auditory prosthesis and the hearing aid are integrated within a hybrid device adapted to be worn at one of the user's ears.

30. The system of claim 1, wherein the auditory prosthesis comprises a cochlear implant arrangement, and wherein the neural stimulation signal is an electric stimulation signal.

31. A method of combined neural and acoustic stimulation of a patient's hearing, comprising
providing an input audio signal,
generating, by a sound processor of an auditory prosthesis, a neural stimulation signal from the input audio signal and stimulating, by an implantable stimulation assembly of the auditory prosthesis, the patient's hearing according to the neural stimulation signal,
processing at least part of the input audio signal by an audio signal processing unit of a hearing aid and stimulating, by an acoustic output transducer of the hearing aid, the patient's hearing according to the processed audio signals, and
communicating, by the auditory prosthesis with the hearing aid, in a manner so as to synchronize a change of at least one parameter used in the generation of the neural stimulation signal with a change of said at least one parameter used in the processing of the input audio signal,
wherein at least one parameter used in the in the processing of the input audio signal is controlled such that, during an adjustment period the value of the at least one parameter is automatically changed from a first value to a second value as a function of a time having passed since a reference point in time.

32. A hearing assistance system comprising an auditory prosthesis device for neural stimulation of a patient's hearing at one of the patient's ears and a hearing aid for acoustic stimulation of the patient's hearing at the same one or the other one of the patient's ears, the system including providing means for providing an input audio signal;
the auditory prosthesis device comprising:
a sound processor for generating a neural stimulation signal from at least part of the input audio signal, and
an implantable stimulation assembly for stimulation of the patient's hearing according to the neural stimulation signal;
the hearing aid comprising:
an audio signal processing unit for processing at least part of the input audio signal,
an acoustic output transducer for stimulating the patient's hearing according to the processed audio signals, and
a control unit for controlling the audio signal processing unit, the control unit being adapted to control at least one parameter used in the processing of the input audio signal such that, during an adjustment period, the value of the at least one parameter is automatically changed from a first value to a second value as a function of time having passed since a reference point in time;
the system further comprising a classifier unit for determining a present auditory scene by analyzing the input audio signal, wherein a duration of the adjustment period depends on the present auditory scene as determined by the classifier unit during the adjustment period.

33. The system of claim 32, wherein the duration of the adjustment period is shorter for auditory scenes with high frequency-averaged input signal levels relative to auditory scenes with low frequency-averaged input signal levels.

34. A method of combined neural and acoustic stimulation of a patient's hearing, comprising
providing an input audio signal,
generating, by a sound processor of an auditory prosthesis, a neural stimulation signal from the input audio signal and stimulating, by an implantable stimulation assembly of the auditory prosthesis, the patient's hearing according to the neural stimulation signal,
processing at least part of the input audio signal by an audio signal processing unit of a hearing aid and stimulating, by an acoustic output transducer of the hearing aid, the patient's hearing according to the processed audio signals,
determining a present auditory scene by analyzing the input audio signal, wherein a duration of the adjustment period depends on the present auditory scene,
wherein at least one parameter used in the in the processing of the input audio signal is controlled such that, during an adjustment period the value of the at least one parameter is automatically changed from a first value to a second value as a function of a time having passed since a reference point in time.

35. The method of claim 34, wherein the duration of the adjustment period is shorter for auditory scenes with high frequency-averaged input signal levels relative to auditory scenes with low frequency-averaged input signal levels.

* * * * *